US012361716B2

(12) United States Patent
Takayanagi

(10) Patent No.: US 12,361,716 B2
(45) Date of Patent: *Jul. 15, 2025

(54) INFORMATION PROCESSING METHOD, RECORDING MEDIUM, AND INFORMATION PROCESSING SYSTEM

(71) Applicant: Panasonic Intellectual Property Management Co., Ltd., Osaka (JP)

(72) Inventor: Tetsuya Takayanagi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,179

(22) Filed: Feb. 13, 2024

(65) Prior Publication Data

US 2024/0185609 A1 Jun. 6, 2024

Related U.S. Application Data

(63) Continuation of application No. 17/005,256, filed on Aug. 27, 2020, now Pat. No. 11,935,301, which is a
(Continued)

(30) Foreign Application Priority Data

Jun. 14, 2018 (JP) ................................ 2018-113438

(51) Int. Cl.
*G06V 20/52* (2022.01)
*G06F 9/54* (2006.01)
(Continued)

(52) U.S. Cl.
CPC .............. *G06V 20/52* (2022.01); *G06F 9/542* (2013.01); *G06T 7/70* (2017.01); *G06V 40/10* (2022.01);
(Continued)

(58) Field of Classification Search
CPC ...... G06V 20/52; G06V 40/10; G06V 40/172; G16H 50/30; G06F 9/542; G06T 7/70; G06T 2207/30201
See application file for complete search history.

(56) References Cited

U.S. PATENT DOCUMENTS 10,198,779 B2 * 2/2019 Pittman .................. G16H 50/80
11,348,371 B2 * 5/2022 Niino ...................... G08B 21/02
(Continued)

FOREIGN PATENT DOCUMENTS

JP 2014-005993 1/2014
WO WO-2011005224 A1 * 1/2011 ............... A61B 5/01

OTHER PUBLICATIONS

Read, et al. (Dynamic social networks and the implications for the spread of infectious disease), pp. 1001-1007. (Year: 2008).*
(Continued)

*Primary Examiner* — Daniel G Mariam
(74) *Attorney, Agent, or Firm* — Wenderoth, Lind & Ponack, L.L.P.

(57) ABSTRACT

An information processing method includes obtaining image information including a first image of a first person in a predetermined facility and a second image of a second person in the predetermined facility; classifying each of the first person and the second person as a resident of the facility or a visitor to the facility, the first person being classified as the resident, the second person being classified as the visitor; calculating a distance between the first person and the second person, based on the first image and the second image; determining whether the first person and the second person are having a conversation with each other, based on the calculated distance; measuring, when it is determined that the first person and the second person are having a conversation with each other, a conversation time during which the first person and the second person are having a
(Continued)

conversation with each other; and transmitting, when the measured conversation time exceeds a predetermined time, infection notification information indicating that a risk of the first person contracting infectious disease is high to a terminal apparatus.

6 Claims, 11 Drawing Sheets

Related U.S. Application Data continuation of application No. PCT/JP2019/020000, filed on May 21, 2019.

(51) Int. Cl.
G06T 7/70 (2017.01)
G06V 40/10 (2022.01)
G06V 40/16 (2022.01)
G16H 50/30 (2018.01)

(52) U.S. Cl.
CPC ........... *G06V 40/172* (2022.01); *G16H 50/30* (2018.01); *G06T 2207/30201* (2013.01)

(56) References Cited

U.S. PATENT DOCUMENTS

| | | | |
|---|---|---|---|
| 11,935,301 B2* | 3/2024 | Takayanagi | G16H 50/30 |
| 2017/0024531 A1* | 1/2017 | Malaviya | G16H 50/30 |
| 2017/0068512 A1* | 3/2017 | Cho | G06F 3/0481 |

OTHER PUBLICATIONS

Computer English Translation of Japanese Patent No. JP2017009825 A, pp. 1-15, 2017.
International Search Report issued Aug. 13, 2019 in International (PCT) Application No. PCT/JP2019/020000.
Jing Yan et al., "Infectious virus in exhaled breath of symptomatic seasonal influenza cases from a college community" PNAS Early Edition, pp. 1-6, Jan. 18, 2018.

* cited by examiner

INFORMATION PROCESSING METHOD, RECORDING MEDIUM, AND INFORMATION PROCESSING SYSTEM

CROSS REFERENCE TO RELATED APPLICATIONS

This is a continuation application of U.S. application Ser. No. 17/005,256 filed on Aug. 27, 2020, which is a continuation application of International (PCT) Application No. PCT/JP2019/020000 filed on May 21, 2019, which claims priority to Japanese Application No. 2018-113438, filed on Jun. 14, 2018. The entire disclosures of the above-identified applications, including the specifications, drawings and claims are incorporated herein by reference in their entirety.

BACKGROUND

1. Technical Field

The present disclosure relates to an information processing method, a recording medium, and an information processing system for issuing a notification of the risk of contracting infectious disease.

2. Description of the Related Art

Many infectious diseases, including influenza, spread from person to person through various routes of infection such as contact infection, droplet infection, and airborne infection. For example, in a space, one infected person infects susceptible persons through a variety of routes of infection. Once an infected person brings infectious disease into a group of susceptible persons, the infectious disease spreads from one susceptible person to another, resulting in the possibility of mass infection. It has been reported that elderly people, children, and other less healthy people are more likely to become seriously ill from any infectious disease, leading to death in the worst case. In particular, in a nursing care facility where elderly people live together, the facility staff takes measures against infectious diseases, such as wearing masks and practicing thorough hand hygiene; however, visitors who come from outside the facility may bring infectious disease, which causes mass infection in the facility.

A technique to address bringing infectious disease from outside is disclosed in, for example, Japanese Unexamined Patent Application Publication No. 2014-5993. The technique includes determining that a person to be authenticated who satisfies a condition in which the time elapsed from entering a room is within a predetermined value is a person coming from outside the room; calculating the cumulative number of persons coming from outside; calculating the number of occupants of the room that the persons enter; dividing the cumulative number of persons coming from outside by the number of occupants of the room to calculate the percentage of the persons coming from outside; and, when the percentage of the persons coming from outside exceeds a predetermined value, setting the relative temperature and the relative humidity of the room to a temperature and humidity that are said to inactivate influenza virus to set the set values for air conditioning control.

Further, according to Jing Yan et al., "Infectious virus in exhaled breath of symptomatic seasonal influenza cases from a college community", PNAS, 2018, cases are reported in which the exhaled breath of an infected individual contains infectious virus.

SUMMARY

In the related art described above, however, it is difficult to estimate the risk of a resident of the facility contracting infectious disease through conversation with a visitor, and further improvement is demanded.

One non-limiting and exemplary embodiment provides a technique for estimating the risk of a resident of a facility contracting infectious disease through conversation with a visitor.

In one general aspect, the techniques disclosed here feature an information processing method executed by a computer, including obtaining image information including a first image of a first person in a predetermined facility and a second image of a second person in the predetermined facility; classifying each of the first person and the second person as a resident of the facility or a visitor to the facility, the first person being classified as the resident, the second person being classified as the visitor; calculating a distance between the first person and the second person, based on the first image and the second image; determining whether the first person and the second person are having a conversation with each other, based on the calculated distance; measuring, when it is determined that the first person and the second person are having a conversation with each other, a conversation time during which the first person and the second person are having a conversation with each other; and transmitting, when the measured conversation time exceeds a predetermined time, infection notification information indicating that a risk of the first person contracting infectious disease is high to a terminal apparatus.

It should be noted that general or specific embodiments may be implemented as an apparatus, a system, an integrated circuit, a computer program, a computer-readable recording medium, or any selective combination of an apparatus, a system, a method, an integrated circuit, a computer program, and a computer-readable recording medium. The computer-readable recording medium includes a non-volatile recording medium such as a compact disc-read only memory (CD-ROM).

According to one embodiment of the present disclosure, it is possible to estimate the risk of a resident of a facility contracting infectious disease through conversation with a visitor and to prevent the resident from contracting infectious disease.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
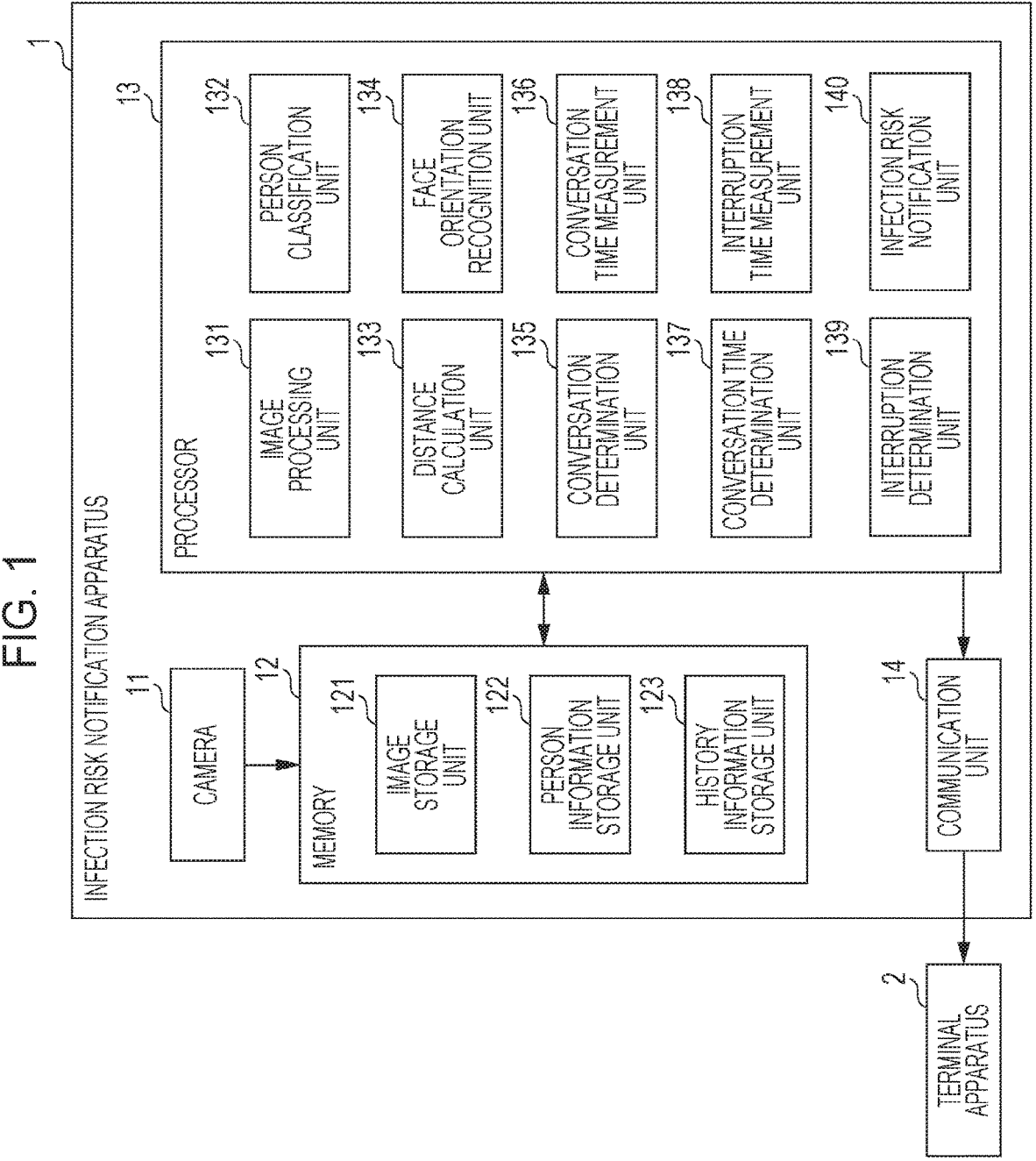
FIG. 1 is a diagram illustrating a configuration of an infection risk notification system according to a first embodiment of the present disclosure.

Underlying Knowledge Forming Basis of the Present Disclosure

In the related art, the cumulative number of persons coming from outside a room is divided by the number of occupants of the room to calculate the percentage of the persons coming from outside, and the statistical risk of infection is evaluated. In the related art, no consideration is given to the risk of infection caused by an interaction between a person coming from outside the room and a person in the room, which is an important process to actually establish infection. A close distance between persons during an interaction means that, if one person is an infected person, the risk of the other person being subjected to contact infection or droplet infection is increased.

In addition, an infected person may exhale infectious virus if they are breathing normally even without coughing or sneezing. Therefore, when people have a conversation in close proximity to each other, the risk of airborne infection, as well as the risk of contact infection and droplet infection, may be increased.

To address the issues described above, an information processing method according to an aspect of the present disclosure is executed by a computer, including obtaining image information including a first image of a first person in a predetermined facility and a second image of a second person in the predetermined facility; classifying each of the first person and the second person as a resident of the facility or a visitor to the facility, the first person being classified as the resident, the second person being classified as the visitor; calculating a distance between the first person and the second person, based on the first image and the second image; determining whether the first person and the second person are having a conversation with each other, based on the calculated distance; measuring, when it is determined that the first person and the second person are having a conversation with each other, a conversation time during which the first person and the second person are having a conversation with each other; and transmitting, when the measured conversation time exceeds a predetermined time, infection notification information indicating that a risk of the first person contracting infectious disease is high to a terminal apparatus. With this configuration, the conversation time during which a resident and a visitor are having a conversation with each other is measured, and, if the measured conversation time exceeds a predetermined time, infection notification information indicating that the risk of the resident contracting infectious disease is high is transmitted to a terminal apparatus. Accordingly, it is possible to estimate the risk of a resident of a facility contracting infectious disease through conversation with a visitor and to prevent the resident from contracting infectious disease.

The information processing method described above may further include obtaining infection information indicating whether the second person is infected with the infectious disease; and changing the predetermined time in accordance with the obtained infection information.

With this configuration, infection information indicating whether the visitor is infected with any infectious disease is obtained, and the predetermined time is changed in accordance with the obtained infection information. Setting the predetermined time to be short when the visitor is infected with any infectious disease and setting the predetermined time to be long when the visitor is not infected with any infectious disease may reduce the risk of the resident contracting infectious disease.

The information processing method described above may further include measuring, when it is determined that the first person and the second person are not having a conversation with each other during measurement of the conversation time, an interruption time during which the conversation between the first person and the second person is interrupted, and the measuring of the conversation time may resume the measurement of the conversation time when the conversation between the first person and the second person is resumed before the measured interruption time exceeds a predetermined time.

With this configuration, when the visitor temporarily moves away from the resident to interrupt the conversation with the resident and then returns to resume the conversation with the resident, the conversation time determined before the conversation is interrupted and the conversation time determined after the conversation is interrupted are added together to measure the total conversation time. Accordingly, it is possible to more accurately estimate the risk of a resident of the facility contracting infectious disease through conversation with a visitor. In the information processing method described above, the determining may determine that the first person and the second person are having a conversation with each other when the distance is less than or equal to a predetermined distance.

With this configuration, it possible to estimate that the resident and the visitor are having a conversation with each other when the distance between the resident and the visitor is short.

The information processing method described above may further include recognizing an orientation of a face of the first person and an orientation of a face of the second person, based on the image information, and the determining may determine that the first person and the second person are having a conversation with each other when the distance is less than or equal to the predetermined distance and when the face of the first person and the face of the second person are facing each other.

With this configuration, it possible to estimate that the resident and the visitor are having a conversation with each other when the distance between the resident and the visitor is short and when the face of the resident and the face of the visitor are facing each other. This may result in more accurate estimation of the risk of the resident contracting infectious disease.

In the information processing method described above, a face image of the first person may be pre-registered, and a face image of the first person that is included in the image information may match the pre-registered face image.

With this configuration, when a face image of a person included in image information matches a pre-registered face image, the person is classified as a resident, and when a face image of a person included in image information does not match a pre-registered face image, the person is classified as a visitor. Registering a face image of each resident in advance may facilitate the classification of a person as a resident or a visitor without registering a face image of any visitor in advance.

A recording medium according to another aspect of the present disclosure stores a program that, when executed by a computer, causes the computer to execute a process, the recording medium being a non-volatile computer-readable recording medium, the process including obtaining image information including a first image of a first person in a predetermined facility and a second image of a second person in the predetermined facility; classifying each of the first person and the second person as a resident of the facility or a visitor to the facility, the first person being classified as the resident, the second person being classified as the visitor; calculating a distance between the first person and the second person, based on the first image and the second image; determining whether the first person and the second person are having a conversation with each other, based on the calculated distance; measuring, when it is determined that the first person and the second person are having a conversation with each other, a conversation time during which the first person and the second person are having a conversation with each other; and transmitting, when the measured conversation time exceeds a predetermined time, infection notification information indicating that a risk of the first person contracting infectious disease is high to a terminal apparatus.

With this configuration, the conversation time during which a resident and a visitor are having a conversation with each other is measured, and, if the measured conversation time exceeds a predetermined time, infection notification information indicating that the risk of the resident contracting infectious disease is high is transmitted to a terminal apparatus. Accordingly, it is possible to estimate the risk of a resident of a facility contracting infectious disease through conversation with a visitor and to prevent the resident from contracting infectious disease.

An information processing system according to another aspect of the present disclosure includes a camera that is installed in a predetermined facility, and an information processing apparatus. The information processing apparatus obtains image information from the camera, the image information including a first image of a first person in the predetermined facility and a second image of a second person in the predetermined facility, classifies each of the first person and the second person as a resident of the facility or a visitor to the facility, the first person being classified as the resident, the second person being classified as the visitor, calculates a distance between the first person and the second person, based on the first image and the second image, determines whether the first person and the second person are having a conversation with each other, based on the calculated distance, measures, when it is determined that the first person and the second person are having a conversation with each other, a conversation time during which the first person and the second person are having a conversation with each other, and transmits, when the measured conversation time exceeds a predetermined time, infection notification information indicating that a risk of the first person contracting infectious disease is high to a terminal apparatus.

With this configuration, the conversation time during which a resident and a visitor are having a conversation with each other is measured, and, if the measured conversation time exceeds a predetermined time, infection notification information indicating that the risk of the resident contracting infectious disease is high is transmitted to a terminal apparatus. Accordingly, it is possible to estimate the risk of a resident of a facility contracting infectious disease through conversation with a visitor and to prevent the resident from contracting infectious disease.

The following describes embodiments of the present disclosure with reference to the drawings. The following embodiments are specific examples of the present disclosure and are not intended to limit the technical scope of the present disclosure.

First Embodiment

FIG. 1 is a diagram illustrating a configuration of an infection risk notification system according to a first embodiment of the present disclosure. The infection risk notification system illustrated in FIG. 1 is an example of an information processing system and includes an infection risk notification apparatus 1 and a terminal apparatus 2.

The infection risk notification apparatus 1 is an example of an information processing apparatus and issues a notification of the risk of contracting infectious disease (infection risk). The infection risk notification apparatus 1 is installed on the wall or ceiling in a predetermined space within a facility. The predetermined space is, for example, a space where a resident and a visitor can communicate with each other, such as a community room in a nursing care facility where many residents gather together or a room where each resident lives. The term "resident" refers to a person who contracts with, for example, a nursing care facility and lives in the nursing care facility. The term "visitor" refers to a person who temporarily visits the facility and can bring infectious disease into the facility. Examples of the visitor include the family of the residents, friends of the residents, and mail and parcel delivery drivers.

The infection risk notification apparatus 1 regards each visitor as an infected person without determining whether the visitor is infected with any infectious disease. When a person suffers from any infectious disease, there is a transition between an infectious period and a symptomatic period, with the two periods being usually different. In the current technology, it is difficult to determine whether a person has an infection before the onset of symptoms, and it is possible to determine that a person is an infected person after a considerable time has passed since the person had an infection. For this reason, the term "infected person" is used to indicate an individual who has been confirmed to have an infection through some measurement such as manifestation of symptoms or diagnosis made by a doctor.

The infection risk notification apparatus 1 is communicably connected to the terminal apparatus 2 via a network. The network is, for example, an intranet or the Internet.

The terminal apparatus 2 is, for example, a personal computer, a smartphone, or a tablet computer. The terminal apparatus 2 is used by, for example, the manager or staff of the facility where residents are located.

The infection risk notification apparatus 1 includes a camera 11, a memory 12, a processor 13, and a communication unit 14.

The camera 11 is installed in a predetermined facility and captures images of a location within the predetermined facility. The camera 11 is an indoor surveillance camera. The camera 11 is installed on the ceiling or the like to detect many residents and visitors, and successively obtains image information of the location within the predetermined facility.

In the first embodiment, the camera 11 may be disposed inside or outside the infection risk notification apparatus 1. When the camera 11 is disposed outside the infection risk notification apparatus 1, the infection risk notification apparatus 1 is communicably connected to the camera 11 via wired or wireless communication.

The memory 12 is, for example, a semiconductor memory and includes an image storage unit 121, a person information storage unit 122, and a history information storage unit 123. The processor 13 includes an image processing unit 131, a person classification unit 132, a distance calculation unit 133, a face orientation recognition unit 134, a conversation determination unit 135, a conversation time measurement unit 136, a conversation time determination unit 137, an interruption time measurement unit 138, an interruption determination unit 139, and an infection risk notification unit 140.

The image storage unit 121 stores image information of images captured using the camera 11. The camera 11 stores image information of captured images of a location within the predetermined facility in the image storage unit 121. The image information may include a first image of a first person in the predetermined facility and a second image of a second person in the predetermined facility.

The image processing unit 131 obtains image information of a captured image of the predetermined space from the image storage unit 121. The image processing unit 131 performs image processing on the obtained image information to extract a person's features, such as the face, eyes, nose, and mouth of a person in a room, the shape of the face, the sizes of the face, eyes, nose, and mouth, the height of the person, the clothes of the person, the orientation of the face, and the position of the person in the room.

The image processing unit 131 extracts a person's features by using machine learning or deep learning. The image processing unit 131 uses, for example, a neural network such as a Convolutional Neural Network (CNN) or a Support Vector Machine (SVM). The use of a neural network enables accurate extraction of a person's features. An algorithm such as CNN or SVM is supervised learning and requires generation of teacher data. The image processing unit 131 may extract a person's features by, for example, using unsupervised clustering as an algorithm in which no teacher data is prepared. The use of an unsupervised algorithm eliminates the need to prepare teacher data in advance, thereby facilitating an implementation into a system.

Further, the image processing unit 131 is capable of identifying an area showing a person contained in the image information. The area showing a person has a rectangular shape, for example. The image processing unit 131 is also capable of identifying the position of the area showing a person in an image and the center-of-gravity position of the area showing a person.

The person information storage unit 122 stores in advance person information in which identification information identifying each resident, the name of the resident, and the features of the resident are associated with one another. Examples of the features of each resident include a face image of the resident.

The person classification unit 132 classifies each of persons contained in the image information as a resident of the facility or a visitor to the facility from the person's features extracted by the image processing unit 131. The person classification unit 132 refers to the person information stored in the person information storage unit 122 and determines whether the person information contains a resident having features that match the person's features extracted by the image processing unit 131. If the person information contains a resident having features that match the person's features extracted by the image processing unit 131, the person classification unit 132 classifies the person contained in the image information as a resident. If the person information does not contain a resident having features that match the person's features extracted by the image processing unit 131, the person classification unit 132 classifies the person contained in the image information as a visitor. That is, a person registered in the person information in advance is classified as a resident, whereas a person not registered in the person information is classified as a visitor.

For example, if a face image of a person included in the image information matches a pre-registered face image of any resident, the person classification unit 132 classifies the person as a resident. If a face image of a person included in the image information does not match a pre-registered face image of any resident, the person is classified as a visitor.

In the person information, identification information identifying the manager and staff of the facility may be associated with the features of the manager and staff of the facility in advance. Accordingly, the manager or staff of the facility can be prevented from being classified as a visitor.

In the person information, furthermore, identification information identifying a visitor may be associated with features of the visitor in advance. In this case, the person classification unit 132 may classify, as a visitor, a person stored in advance as a visitor in the person information among persons contained in the image information. This ensures that the person can be classified as a resident or a visitor.

Supervised learning may be performed using images of residents to generate a neural network model. The person classification unit 132 may input the obtained image information to the neural network model to classify a person contained in the image information as a resident. During learning, the face and name of each resident may be associated with each other in advance.

Accordingly, name information of a resident can also be obtained when classified.

The distance calculation unit 133 calculates a distance between a resident and a visitor who are classified by the person classification unit 132. The distance calculation unit 133 estimates the distance between the resident and the visitor from the position coordinates of the resident and the position coordinates of the visitor. To calculate the distance between the resident and the visitor, for example, the Euclidean distance between the center-of-gravity position of an area showing the detected resident and the center-of-gravity position of an area showing the visitor may be calculated. The center-of-gravity position of an area showing a person contained in the image information is detected by the image processing unit 131. A person contained in the image information is classified as a resident or a visitor by the person classification unit 132.

Alternatively, lattice patterns whose sizes and positions are known may be placed in the predetermined space. The distance calculation unit 133 may perform camera calibration on the basis of the sizes and positions of the lattice patterns, which are included in the image information. Camera calibration enables accurate calculation of a distance between a resident and a visitor without dependence on the distances between the camera 11 and the persons. The calculated distance is output to the conversation determination unit 135.

The face orientation recognition unit 134 recognizes the orientation of the face of the resident and the orientation of the face of the visitor on the basis of the image information. The face orientation recognition unit 134 is capable of identifying the direction in which the face of the resident is oriented and the direction in which the face of the visitor is oriented, from the person's features extracted by the image processing unit 131.

The conversation determination unit 135 determines whether the resident and the visitor are having a conversation with each other on the basis of the distance calculated by the distance calculation unit 133. If the distance between the resident and the visitor is less than or equal to a predetermined distance and the face of the resident and the face of the visitor are facing each other, the conversation determination unit 135 determines that the resident and the visitor are having a conversation with each other. The predetermined distance may be, for example, a value less than or equal to 1 meter.

In this way, the determination of whether the face of a resident and the face of a visitor are facing each other can prevent erroneous detection of a visitor who is in close proximity to the resident, but who is not having a conversation with the resident.

If the conversation determination unit 135 determines that the resident and the visitor are having a conversation with each other, the conversation time measurement unit 136 measures the conversation time during which the resident and the visitor are having a conversation with each other.

When persons are within a distance less than or equal to the predetermined distance, this may indicate that the persons have approached each other to perform communication such as having a conversation with each other. Accordingly, the conversation time measurement unit 136 accumulates the time during which the distance between the resident and the visitor is less than or equal to the predetermined distance and during which the face of the resident and the face of the visitor are facing each other, as the time during which the resident and the visitor are having a conversation with each other, and measures the conversation time.

The conversation time determination unit 137 determines whether the conversation time measured by the conversation time measurement unit 136 exceeds a predetermined time. The predetermined time may be, for example, 20 minutes. That is, eliminating a short time period, such as about 5 minutes to 10 minutes, from the predetermined time to be compared with the conversation time can reduce the burden on the manager or staff of the facility.

If it is determined that the resident and the visitor are not having a conversation during the measurement of the conversation time, the interruption time measurement unit 138 measures the interruption time during which the conversation between the resident and the visitor is interrupted.

The interruption determination unit 139 determines whether the measured interruption time exceeds a predetermined time.

If the conversation between the resident and the visitor is resumed before the interruption time measured by the interruption time measurement unit 138 exceeds the predetermined time, the conversation time measurement unit 136 resumes the measurement of the conversation time. The predetermined time is, for example, 5 minutes.

For example, the visitor may temporarily leave to take a telephone call or the like during the conversation and then return after the lapse of a short time period such as 5 minutes. Accordingly, if the distance between the resident and the visitor who have had a conversation with each other is determined to be longer than the predetermined distance and is then determined to be less than or equal to the predetermined distance again within a predetermined time, the conversation time measurement unit 136 may add together the conversation time determined before the conversation is interrupted and the conversation time determined after the conversation is interrupted. This enables accurate measurement of the total conversation time even if either person leaves for a short time during the conversation. The measured conversation time is accumulated in the memory 12 and is sequentially updated.

The history information storage unit 123 stores history information in which identification information identifying each resident, the place in which the resident is located, a conversation start time indicating the time when the conversation with a visitor is started, a conversation end time indicating the time when the conversation with the visitor is terminated, visitor information indicating the features of the visitor with whom the resident has had a conversation, infection information indicating whether the visitor is infected, a conversation start flag indicating that a conversation with a visitor has started, and an infection risk flag indicating that the risk of contracting infectious disease is increased due to the conversation time exceeding the predetermined time are associated with one another. The visitor information indicates, for example, the gender, height, and age of the corresponding visitor and is obtained from the person's features extracted by the image processing unit 131.

If the conversation determination unit 135 determines that the resident and the visitor are having a conversation with each other, the conversation time measurement unit 136 stores in the history information storage unit 123 identification information identifying the resident, the place in which the resident is located, the conversation start time, visitor information, infection information, and the conversation start flag. If it is determined that the measured interruption time exceeds the predetermined time, the interruption determination unit 139 stores in the history information storage unit 123 the time when the conversation is terminated.

Further, the communication unit 14 may obtain infection information indicating whether the visitor is infected with any infectious disease. The infection information is input and transmitted together with information identifying the visitor by, for example, a doctor, the staff, or the visitor themselves. An infrared camera at the entrance of the facility may measure the temperature of a visitor entering the facility. If it is determined that the temperature of a visitor entering the facility, which is measured by the infrared camera, is greater than or equal to a predetermined temperature, the processor 13 may store in the memory 12 a face image of the visitor and infection information indicating that the visitor is infected with any infectious disease.

The conversation time determination unit 137 may change the predetermined time, which is used to determine the conversation time, in accordance with the obtained infection information. That is, the conversation time determination unit 137 may set a predetermined time for the case where infection information of a visitor with whom a resident is having a conversation indicates that the visitor is infected with any infectious disease to be shorter than a predetermined time for the case where infection information of the visitor with whom the resident is having a conversation indicates that the visitor is not infected with any infectious disease. This enables more appropriate evaluation of the infection risk of the resident.

If the measured conversation time exceeds the predetermined time, the infection risk notification unit 140 generates infection notification information indicating that the risk of the resident contracting infectious disease is high, and instructs the communication unit 14 to transmit the generated infection notification information to the terminal apparatus 2.

The communication unit 14 transmits the infection notification information generated by the infection risk notification unit 140 to the terminal apparatus 2. The terminal apparatus 2 receives the infection notification information transmitted from the communication unit 14. The terminal apparatus 2 displays the received infection notification information.

In this way, if the conversation time exceeds the predetermined time, the infection risk notification unit 140 determines that the infection risk of the resident may be high, and outputs infection notification information to the communication unit 14. The infection notification information includes information such as the place in which the resident is located, the conversation start time, and the name of the resident. Since the features of the visitor are also extracted from the image information, the infection risk notification unit 140 may generate the infection notification information that includes information indicating the features of the visitor. This allows the staff or manager of the facility to later keep track of the detailed point in time when the infection risk was increased. Further, the communication unit 14 transmits the infection notification information to the terminal apparatus 2 of the staff or manager of the facility. This allows the staff or manager of the facility to know a resident whose infection risk is high in real time, and also to take measures as necessary upon receipt of the infection notification information.

In the first embodiment, the conversation determination unit 135 determines that a resident and a visitor are having a conversation with each other when the distance between the resident and the visitor is less than or equal to a predetermined distance and when the face of the resident and the face of the visitor are facing each other; however, the present disclosure is not limited thereto. The conversation determination unit 135 may determine that a resident and a visitor are having a conversation with each other when the distance between the resident and the visitor is less than or equal to a predetermined distance without determining whether the face of the resident and the face of the visitor are facing each other.

The operation of the infection risk notification apparatus 1 according to the first embodiment will now be described.

Figure 2:
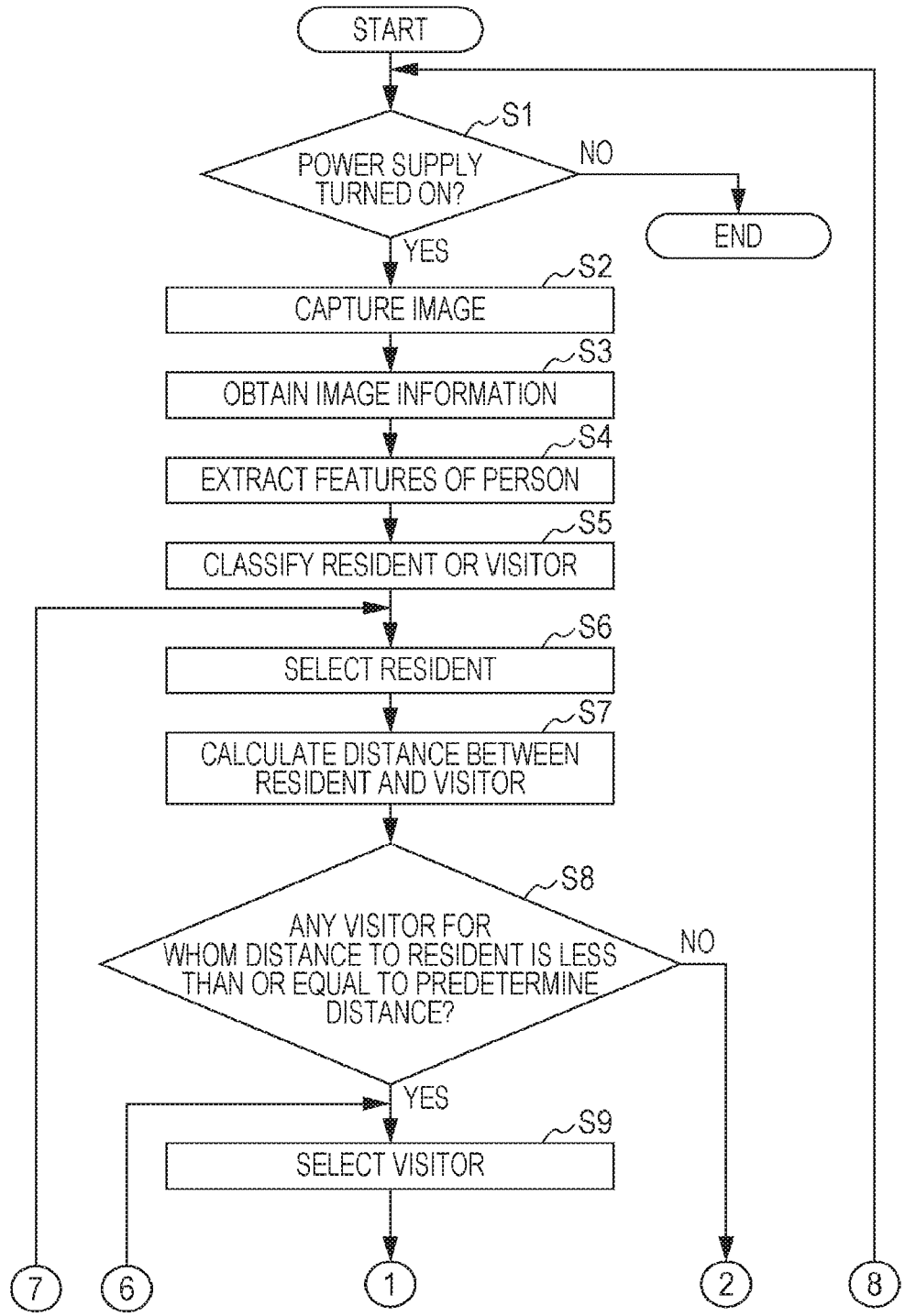
FIG. 2 is a first portion of a flowchart illustrating the operation of an infection risk notification apparatus according to the first embodiment.
Figure 3:
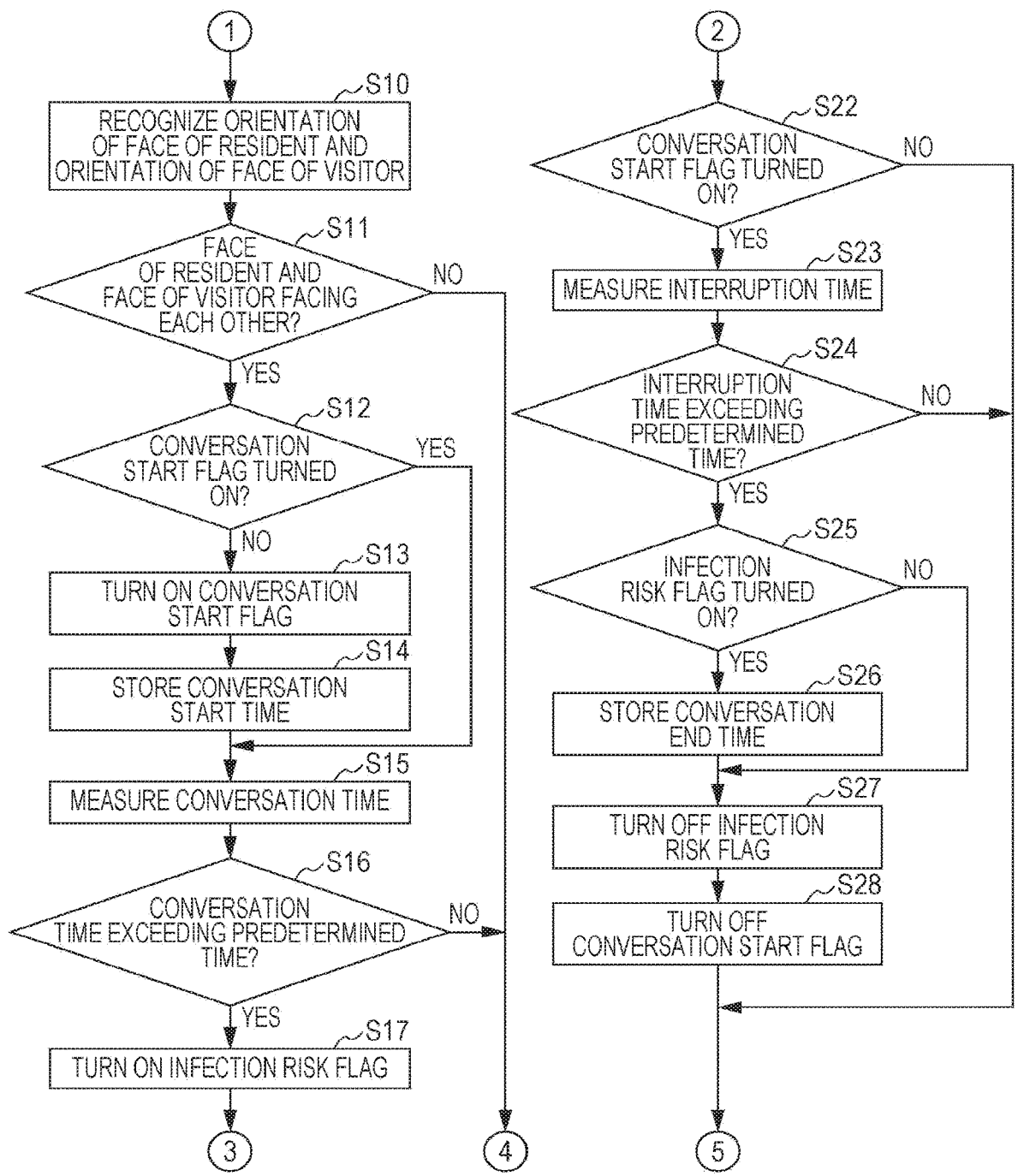
FIG. 3 is a second portion of the flowchart illustrating the operation of the infection risk notification apparatus according to the first embodiment.
Figure 4:
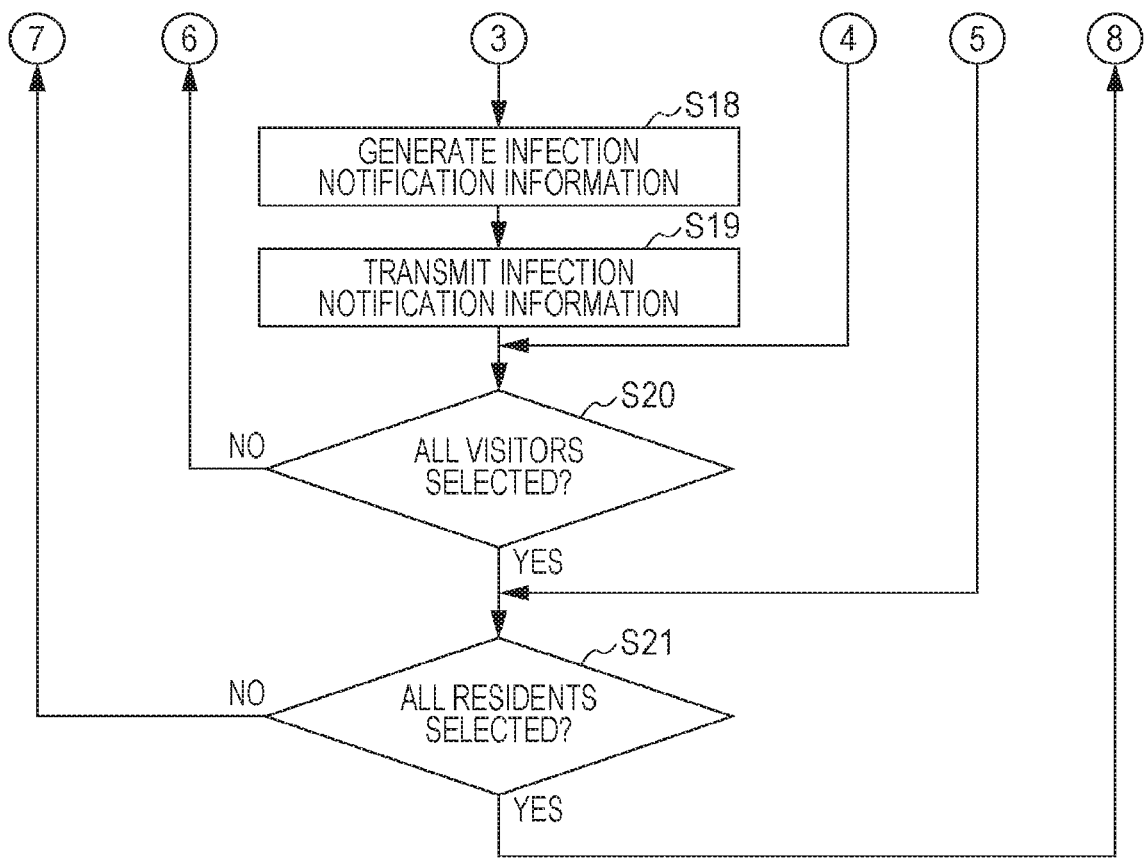
FIG. 4 is a third portion of the flowchart illustrating the operation of the infection risk notification apparatus according to the first embodiment.

FIG. 2 is a first portion of a flowchart illustrating the operation of the infection risk notification apparatus 1 according to the first embodiment, FIG. 3 is a second portion of the flowchart illustrating the operation of the infection risk notification apparatus 1 according to the first embodiment, and FIG. 4 is a third portion of the flowchart illustrating the operation of the infection risk notification apparatus 1 according to the first embodiment.

First, in step S1, the processor 13 determines whether power supply to the infection risk notification apparatus 1 is turned on. If it is determined that power supply to the infection risk notification apparatus 1 is turned off (NO in step S1), the process ends.

On the other hand, if it is determined that power supply to the infection risk notification apparatus 1 is turned on (YES in step S1), in step S2, the camera 11 captures an image of a predetermined space within the facility. The camera 11 stores image information of the captured image in the image storage unit 121. In this case, the camera 11 stores a moving image in the image storage unit 121.

Then, in step S3, the image processing unit 131 obtains the image information from the image storage unit 121.

Then, in step S4, the image processing unit 131 extracts the features of a person from the image information. The features of a person include, for example, the face, eyes, nose, mouth of a person in a room, the shape of the face, the sizes of the face, eyes, nose, and mouth, the height of the person, the clothes of the person, the orientation of the face, and the position of the person in the room.

Then, in step S5, the person classification unit 132 classifies a person contained in the image information as a resident of the facility or a visitor to the facility, from the person's features extracted by the image processing unit 131. A face image of each resident is pre-registered in the person information storage unit 122. If a face image of a person included in the image information, which is extracted by the image processing unit 131, matches any pre-registered face image, the person classification unit 132 classifies the person as a resident. If a face image of a person included in the image information, which is extracted by the image processing unit 131, does not match any pre-registered face image, the person classification unit 132 classifies the person as a visitor.

The person classification unit 132 may classify the person as a resident or a visitor by using a neural network model obtained in advance from machine learning.

Then, in step S6, the distance calculation unit 133 selects the resident classified by the person classification unit 132. If residents are classified by the person classification unit 132, the distance calculation unit 133 selects one of the residents. If a single resident is classified by the person classification unit 132, the distance calculation unit 133 selects the single resident. If no resident is classified by the person classification unit 132, that is, if the image information contains no resident, the process may return to step S1.

Then, in step S7, the distance calculation unit 133 calculates the distance between the selected resident and the visitor. If visitors are classified by the person classification unit 132, the distance calculation unit 133 calculates the distance between the selected resident and each of the visitors. In this case, the distance calculation unit 133 calculates the Euclidean distance between the center-of-gravity position of an area showing the resident and the center-of-gravity position of an area showing each of the visitors.

Then, in step S8, the conversation determination unit 135 determines whether there is any visitor for whom the distance to the selected resident is less than or equal to a predetermined distance on the basis of the distance calculated by the distance calculation unit 133.

If it is determined that there is any visitor for whom the distance to the selected resident is less than or equal to the predetermined distance (YES in step S8), in step S9, the conversation determination unit 135 selects a visitor for whom the distance to the selected resident is less than or equal to the predetermined distance. If there are visitors for whom the distances to the selected resident are less than or equal to the predetermined distance, the conversation determination unit 135 selects one of the visitors. For example, the conversation determination unit 135 selects one of the visitors who is the closest to the selected resident.

Then, in step S10, the face orientation recognition unit 134 recognizes the orientation of the face of the selected resident and the orientation of the face of the selected visitor on the basis of the image information. The orientation of the face of the resident and the orientation of the face of the visitor are represented by vectors, for example.

Then, in step S11, the conversation determination unit 135 determines whether the face of the selected resident and the face of the selected visitor are facing each other. The face of the resident and the face of the visitor need not be completely facing each other. The conversation determination unit 135 may determine that the face of the resident and the face of the visitor are facing each other when the angle defined by the vector indicating the orientation of the face of the resident and the vector indicating the orientation of the face of the visitor is less than or equal to a predetermined angle. If it is determined that the face of the selected resident and the face of the selected visitor are not facing each other (NO in step S11), the process proceeds to step S20.

On the other hand, if it is determined that the face of the selected resident and the face of the selected visitor are facing each other (YES in step S11), in step S12, the conversation time measurement unit 136 determines whether the conversation start flag corresponding to the selected resident is turned on in the history information of the selected resident that is stored in the history information storage unit 123.

If it is determined that the conversation start flag corresponding to the selected resident is turned on (YES in step S12), the process proceeds to step S15.

On the other hand, if it is determined that the conversation start flag corresponding to the selected resident is not turned on (NO in step S12), in step S13, the conversation time measurement unit 136 turns on the conversation start flag corresponding to the selected resident.

Then, in step S14, the conversation time measurement unit 136 stores the current time in the history information storage unit 123 as the conversation start time.

Then, in step S15, the conversation time measurement unit 136 measures the conversation time during which the selected resident and the selected visitor are having a conversation with each other. Since the conversation start time is stored in the history information storage unit 123, the conversation time measurement unit 136 calculates a time period from the conversation start time to the current time to measure the conversation time during which the selected resident and the selected visitor are having a conversation with each other.

Then, in step S16, the conversation time determination unit 137 determines whether the conversation time measured by the conversation time measurement unit 136 exceeds a predetermined time. If it is determined that the conversation time does not exceed the predetermined time (NO in step S16), the process proceeds to step S20.

On the other hand, if it is determined that the conversation time exceeds the predetermined time (YES in step S16), in step S17, the conversation time determination unit 137 turns on the infection risk flag corresponding to the selected resident.

Then, in step S18, the infection risk notification unit 140 generates infection notification information indicating that the risk of the selected resident contracting infectious disease is high.

Then, in step S19, the communication unit 14 transmits the infection notification information generated by the infection risk notification unit 140 to the terminal apparatus 2. The terminal apparatus 2 receives the infection notification information transmitted from the communication unit 14. The terminal apparatus 2 displays the received infection notification information.

Figure 5:
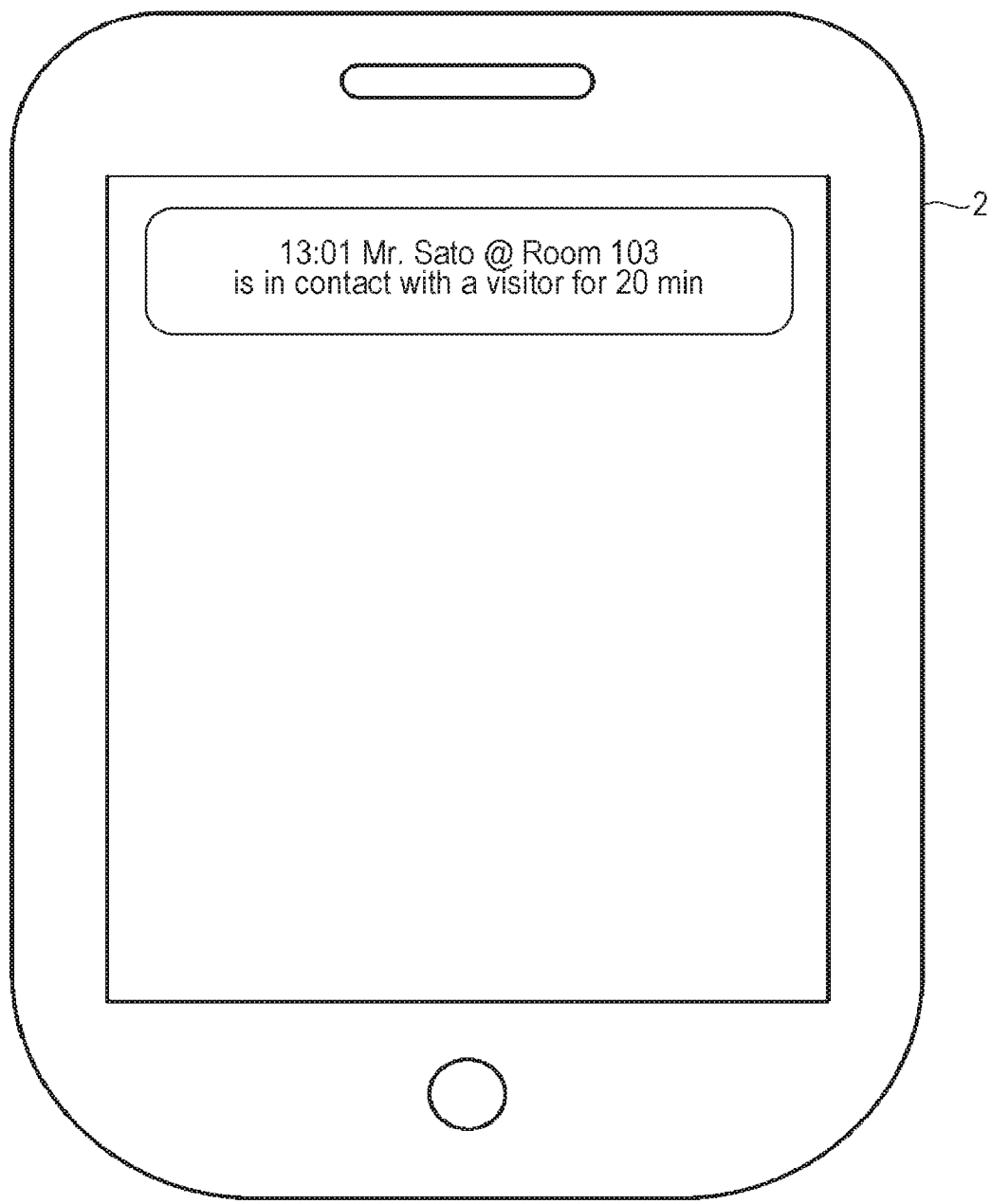
FIG. 5 is a diagram illustrating an example of infection notification information displayed on a terminal apparatus according to the first embodiment.

FIG. 5 is a diagram illustrating an example of the infection notification information displayed on the terminal apparatus 2 according to the first embodiment.

The infection notification information includes the time when the duration of a conversation between each resident and a visitor reaches a predetermined time, the name of the resident, the place in which the resident is located, and the duration of the conversation with the visitor. In FIG. 5, the name of the resident having a conversation with the visitor is "Mr. Sato", and the place in which the resident is located is "Room 103". As of 13:01, the duration of the conversation with the visitor has reached the predetermined time. Thus, the lapse of the predetermined time from the start of the conversation with the visitor is displayed on the display screen of the terminal apparatus 2. The information included in the infection notification information described above is an example.

The terminal apparatus 2 may display history information. To have more detailed information about the infection risk, the staff of the facility taps the display screen illustrated in FIG. 5 with a finger, for example. When the display screen is tapped, the terminal apparatus 2 transmits to the infection risk notification apparatus 1 a request signal for requesting transmission of history information. Upon receipt of the request signal transmitted from the terminal apparatus 2, the communication unit 14 of the infection risk notification apparatus 1 reads history information stored in the history information storage unit 123 and transmits the read history information to the terminal apparatus 2.

Figure 6:
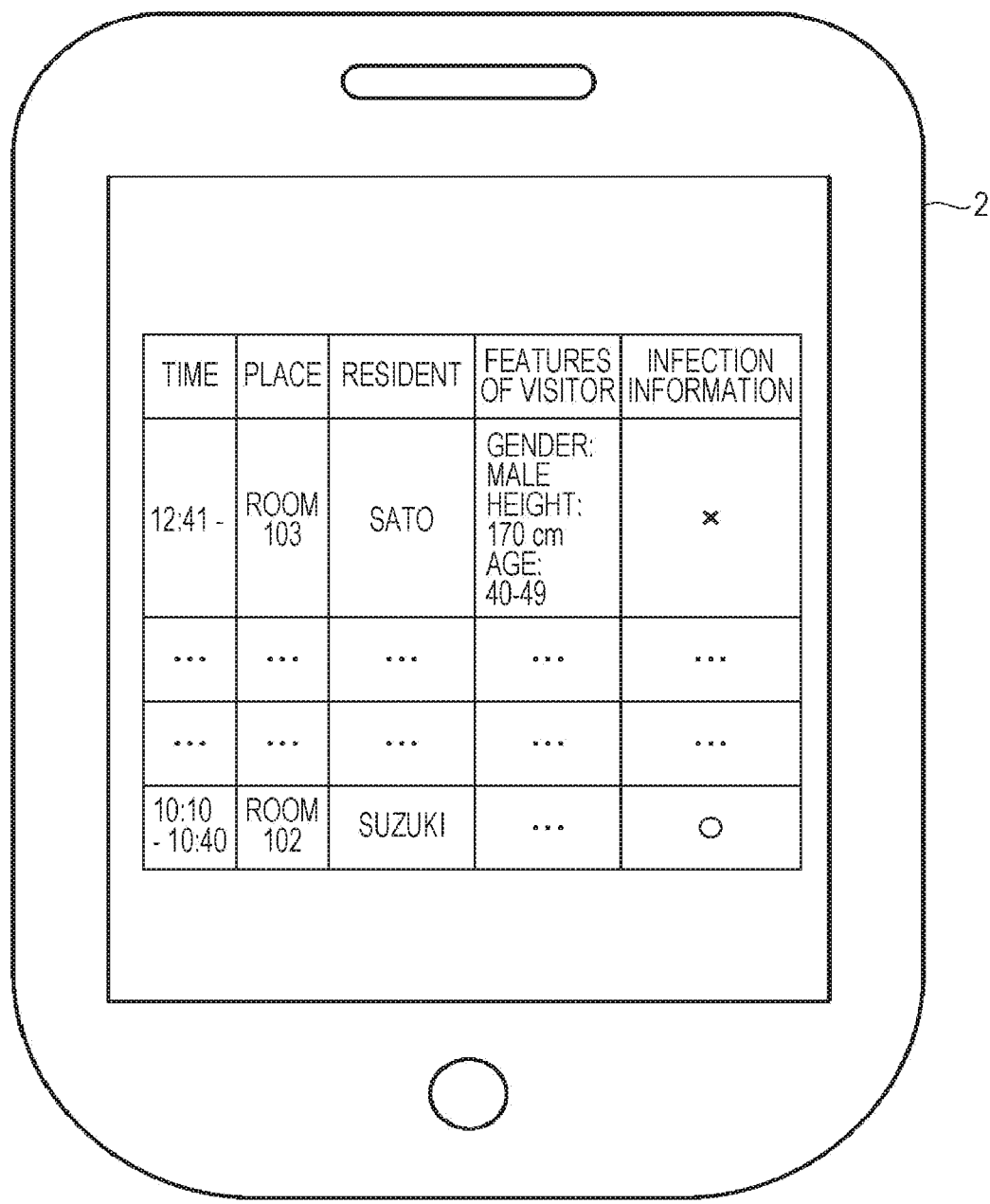
FIG. 6 is a diagram illustrating an example of history information displayed on the terminal apparatus according to the first embodiment.

FIG. 6 is a diagram illustrating an example of the history information displayed on the terminal apparatus 2 according to the first embodiment.

The history information includes a conversation start time, a conversation end time, the name of each resident, the place in which the resident is located, features of each visitor, and infection information of the visitor. As illustrated in FIG. 6, history information is collected into a spreadsheet, thereby facilitating the management of the history information.

In FIG. 6, the most recent event is displayed in the topmost spreadsheet row. In FIG. 6, the display screen of the terminal apparatus 2 shows that the place in which the resident associated with the most recent event is located is "Room 103", the name of the resident having a conversation with a visitor is "Sato", and the conversation start time is "12:41". The display screen also shows features of the visitor, including the gender of the visitor, the height of the visitor, and the age of the visitor. The features of each visitor are estimate values based on features extracted from the image information, and are not actually measured values.

The display screen further shows infection information of each visitor. The infection information is information indicating whether a visitor having a conversation with a resident is infected with any infectious disease. A circle is presented for a visitor infected with any infectious disease, and a cross is presented for a visitor not infected with any infectious disease. The infection information is given in advance on the basis of a doctor's diagnostic result or sensing information. In FIG. 6, a conversation time is presented regardless of whether the visitor is infected with any infectious disease; however, the present disclosure is not limited thereto. If it is known in advance whether each of the visitors is infected with any infectious disease, a resident having a conversation with an infected visitor may be the target for which a notification of the infection risk is to be issued. In this case, the "infection information" column is unnecessary. The information included in the history information described above is an example.

Referring back to FIG. 4, in step S20, the conversation determination unit 135 determines whether all of the visitors for whom the distances to the selected resident are less than or equal to the predetermined distance have been selected. That is, if there are visitors for whom the distances to the selected resident are less than or equal to the predetermined distance, the conversation determination unit 135 determines whether there is any unselected visitor among the visitors. If it is determined that not all of the visitors for whom the distances to the selected resident are less than or equal to the predetermined distance have been selected (NO in step S20), the process returns to step S9.

In step S9, the conversation determination unit 135 selects a visitor for whom the distance to the selected resident is less than or equal to the predetermined distance and who remains unselected. For example, the conversation determination unit 135 selects a visitor from among the visitors in order from the closest to the selected resident.

On the other hand, if it is determined that all of the visitors for whom the distances to the selected resident are less than or equal to the predetermined distance have been selected (YES in step S20), in step S21, the conversation determination unit 135 determines whether all the residents classified by the person classification unit 132 have been selected. That is, if residents are classified by the person classification unit 132, the conversation determination unit 135 determines whether there is any unselected resident among the residents. If it is determined that not all of the classified residents have been selected (NO in step S21), the process returns to step S6.

On the other hand, if it is determined that all of the classified residents have been selected (YES in step S21), the process returns to step S1.

If it is determined in step S8 that there is no visitor for whom the distance to the resident is less than or equal to the predetermined distance (NO in step S8), in step S22, the interruption determination unit 139 determines whether the conversation start flag corresponding to the selected resident is turned on in the history information of the selected resident, which is stored in the history information storage unit 123.

If it is determined that the conversation start flag corresponding to the selected resident is not turned on (NO in step S22), the process proceeds to step S21.

On the other hand, if it is determined that the conversation start flag corresponding to the selected resident is turned on (YES in step S22), in step S23, the interruption time measurement unit 138 measures the interruption time during which the conversation between the resident and the visitor is interrupted. When starting the measurement of the interruption time, the interruption time measurement unit 138 stores in the memory 12 an interruption start time indicating the time of starting the measurement of the interruption time. Since the interruption start time is stored in the memory 12, the interruption time measurement unit 138 calculates a time period from the interruption start time to the current time to measure the interruption time during which the conversation between the resident and the visitor is interrupted.

Then, in step S24, the interruption determination unit 139 determines whether the measured interruption time exceeds a predetermined time. If it is determined that the measured interruption time does not exceed the predetermined time (NO in step S24), the process proceeds to step S21.

On the other hand, if it is determined that the measured interruption time exceeds the predetermined time (YES in step S24), in step S25, the interruption determination unit 139 determines whether the infection risk flag is turned on. If it is determined that the infection risk flag is not turned on, that is, if the infection risk flag is turned off (NO in step S25), the process proceeds to step S27.

On the other hand, if it is determined that the infection risk flag is turned on (YES in step S25), in step S26, the interruption determination unit 139 stores the interruption start time in the history information storage unit 123 as the conversation end time.

Then, in step S27, the interruption determination unit 139 turns off the infection risk flag corresponding to the selected resident in the history information of the selected resident.

Then, in step S28, the interruption determination unit 139 turns off the conversation start flag corresponding to the selected resident in the history information of the selected resident. After the processing of step S28, the process proceeds to step S21.

In this way, the conversation time during which a resident and a visitor are having a conversation with each other is measured, and, if the measured conversation time exceeds a predetermined time, infection notification information indicating that the risk of the resident contracting infectious disease is high is transmitted to the terminal apparatus 2. Accordingly, it is possible to estimate the risk of a resident of a facility contracting infectious disease through conversation with a visitor and to prevent the resident from contracting infectious disease.

Second Embodiment

In the first embodiment, the infection risk notification apparatus 1 includes the camera 11. In a second embodiment, in contrast, an infection risk notification apparatus includes no camera and is communicably connected to a camera.

Figure 7:
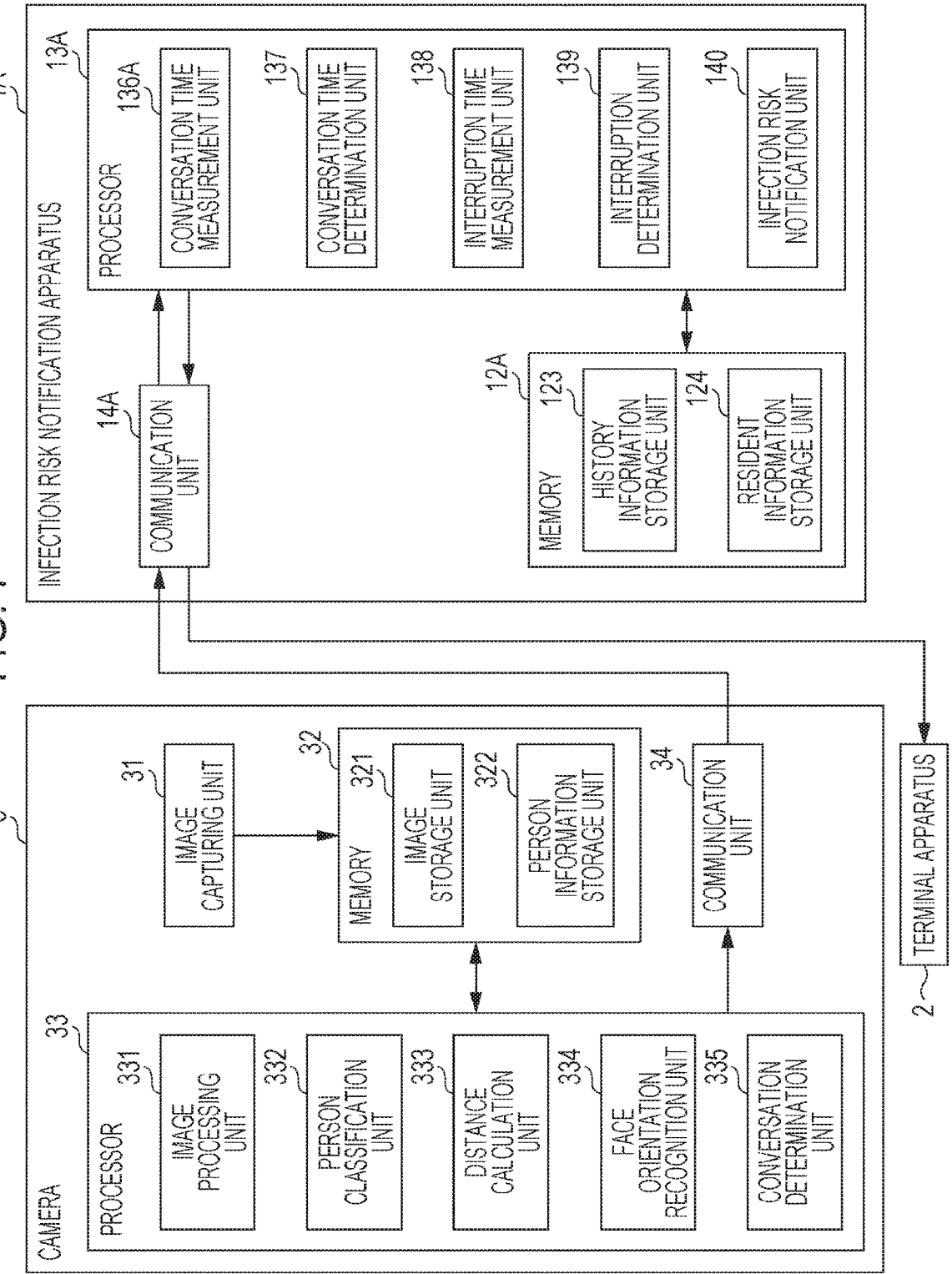
FIG. 7 is a diagram illustrating a configuration of an infection risk notification system according to a second embodiment of the present disclosure.

FIG. 7 is a diagram illustrating a configuration of an infection risk notification system according to the second embodiment of the present disclosure. The infection risk notification system illustrated in FIG. 7 includes an infection risk notification apparatus 1A, a terminal apparatus 2, and a camera 3. In the second embodiment, the same components as those in the first embodiment are denoted by the same numerals and will not be described in detail.

The camera 3 is installed on the ceiling or wall in a predetermined space within a facility. The camera 3 is communicably connected to the infection risk notification apparatus 1A via a network. The camera 3 includes an image capturing unit 31, a memory 32, a processor 33, and a communication unit 34.

The image capturing unit 31 is, for example, an imaging element. The image capturing unit 31 captures an image of the predetermined space and outputs image information of the captured image to the memory 32.

The memory 32 is, for example, a semiconductor memory and includes an image storage unit 321 and a person information storage unit 322. The image storage unit 321 stores image information of images captured using the image capturing unit 31. The image capturing unit 31 stores image information of a captured image of the predetermined space in the image storage unit 321.

The processor 33 includes an image processing unit 331, a person classification unit 332, a distance calculation unit 333, a face orientation recognition unit 334, and a conversation determination unit 335.

The image processing unit 331 obtains image information of a captured image of the predetermined space from the image storage unit 321. The image processing unit 331 performs image processing on the obtained image information to extract a person's features, such as the face, eyes, nose, and mouth of a person in a room, the shape of the face, the sizes of the face, eyes, nose, and mouth, the height of the person, the clothes of the person, the orientation of the face, and the position of the person in the room. The image processing unit 331 extracts a person's features by using machine learning or deep learning.

The functions of the image processing unit 331 are the same as the functions of the image processing unit 131 according to the first embodiment.

The person information storage unit 322 stores in advance person information in which identification information identifying each resident, the name of the resident, and the features of the resident are associated with one another. Examples of the features of each resident include a face image of the resident. The person classification unit 332 classifies each of persons contained in the image information as a resident of the facility or a visitor to the facility from the person's features extracted by the image processing unit 331. The functions of the person classification unit 332 are the same as the functions of the person classification unit 132 according to the first embodiment.

The distance calculation unit 333 calculates a distance between a resident and a visitor, who are classified by the person classification unit 332. The functions of the distance calculation unit 333 are the same as the functions of the distance calculation unit 133 according to the first embodiment.

The face orientation recognition unit 334 recognizes the orientation of the face of the resident and the orientation of the face of the visitor on the basis of the image information. The face orientation recognition unit 334 is capable of identifying the direction in which the face of the resident is oriented and the direction in which the face of the visitor is oriented, from the person's features extracted by the image processing unit 331. The functions of the face orientation recognition unit 334 are the same as the functions of the face orientation recognition unit 134 according to the first embodiment.

The conversation determination unit 335 determines whether the resident and the visitor are having a conversation with each other on the basis of the distance calculated by the distance calculation unit 333. If the distance between the resident and the visitor is less than or equal to a predetermined distance and the face of the resident and the face of the visitor are facing each other, the conversation determination unit 335 determines that the resident and the visitor are having a conversation with each other. The predetermined distance may be, for example, a value less than or equal to 1 meter. The functions of the conversation determination unit 335 are the same as the functions of the conversation determination unit 135 according to the first embodiment.

When the conversation determination unit 335 determines that the resident and the visitor are having a conversation with each other, the conversation determination unit 335 generates a conversation flag information and outputs the generated conversation flag information to the communication unit 34. The conversation flag information includes, for example, identification information such as a name and a number for identifying a resident having a conversation with a visitor, the place in which the resident is located, the current time, and visitor information indicating the features of the visitor. The visitor information indicates, for example, the gender, height, and age of the visitor and is obtained from the person's features extracted by the image processing unit 331. The memory 32 stores in advance the location where the camera 3 is installed. The conversation determination unit 335 generates the conversation flag information that also includes the location where the camera 3 is installed as the place in which the resident is located.

The communication unit 34 transmits the conversation flag information output from the conversation determination unit 335 to the infection risk notification apparatus 1A.

The infection risk notification apparatus 1A issues a notification of the risk of the resident contracting infectious disease. The infection risk notification apparatus 1A may be installed in any location. The infection risk notification apparatus 1A may be a server, for example. The infection risk notification apparatus 1A is communicably connected to the terminal apparatus 2 and the camera 3 via a network.

The infection risk notification apparatus 1A includes a memory 12A, a processor 13A, and a communication unit 14A.

The memory 12A is, for example, a semiconductor memory and includes the history information storage unit 123 and a resident information storage unit 124. The processor 13A includes a conversation time measurement unit 136A, the conversation time determination unit 137, the interruption time measurement unit 138, the interruption determination unit 139, and the infection risk notification unit 140.

The communication unit 14A receives the conversation flag information transmitted from the camera 3. The communication unit 14A transmits the infection notification information generated by the infection risk notification unit 140 to the terminal apparatus 2.

The resident information storage unit 124 stores identification information such as a name and a number for identifying each resident of the facility.

Upon receipt of the conversation flag information at the communication unit 14A, the conversation time measurement unit 136A measures the conversation time during which the resident and the visitor are having a conversation with each other. The conversation time measurement unit 136A accumulates the time of receipts of conversation flag information transmitted when the distance between the resident and the visitor is less than or equal to a predetermined distance and when the face of the resident and the face of the visitor are facing each other, as the time during which the resident and the visitor are having a conversation with each other, and measures a conversation time.

The operation of the infection risk notification apparatus 1A and the camera 3 according to the second embodiment will now be described.

Figure 8:
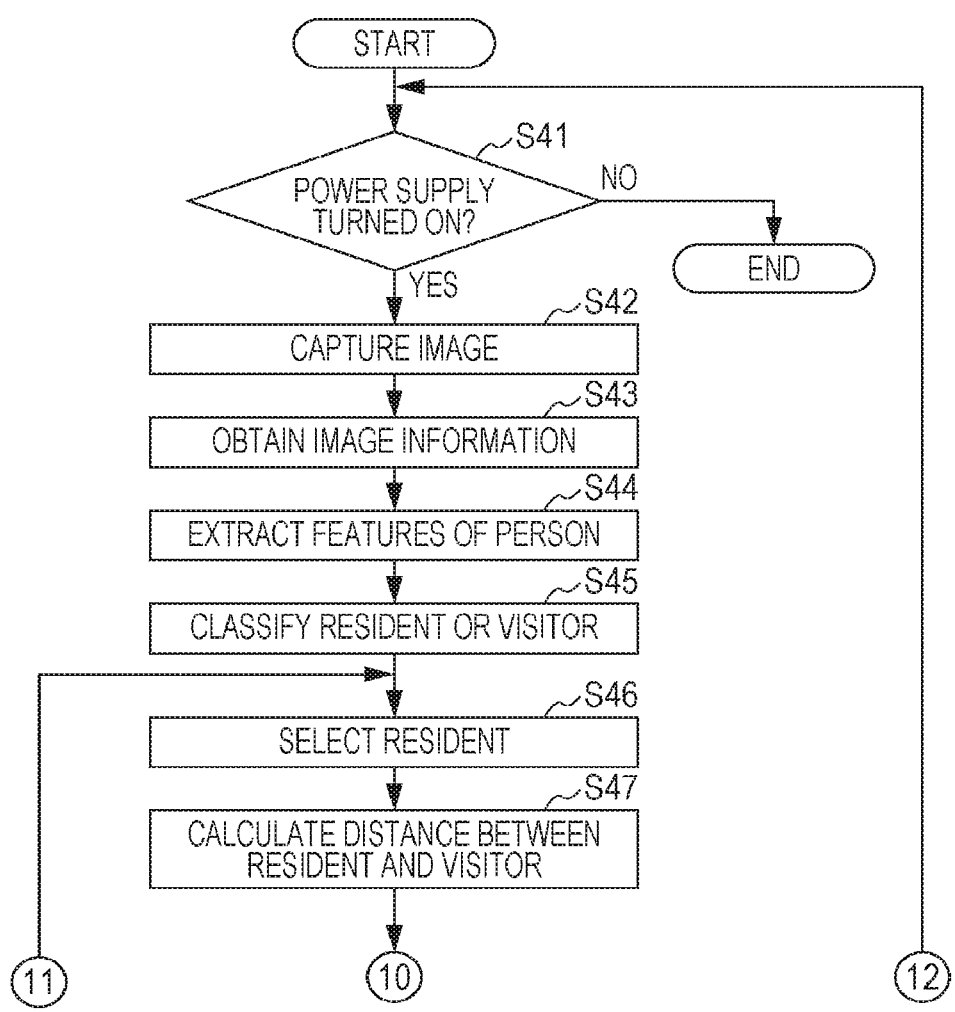
FIG. 8 is a first portion of a flowchart illustrating the operation of a camera according to the second embodiment.
Figure 9:
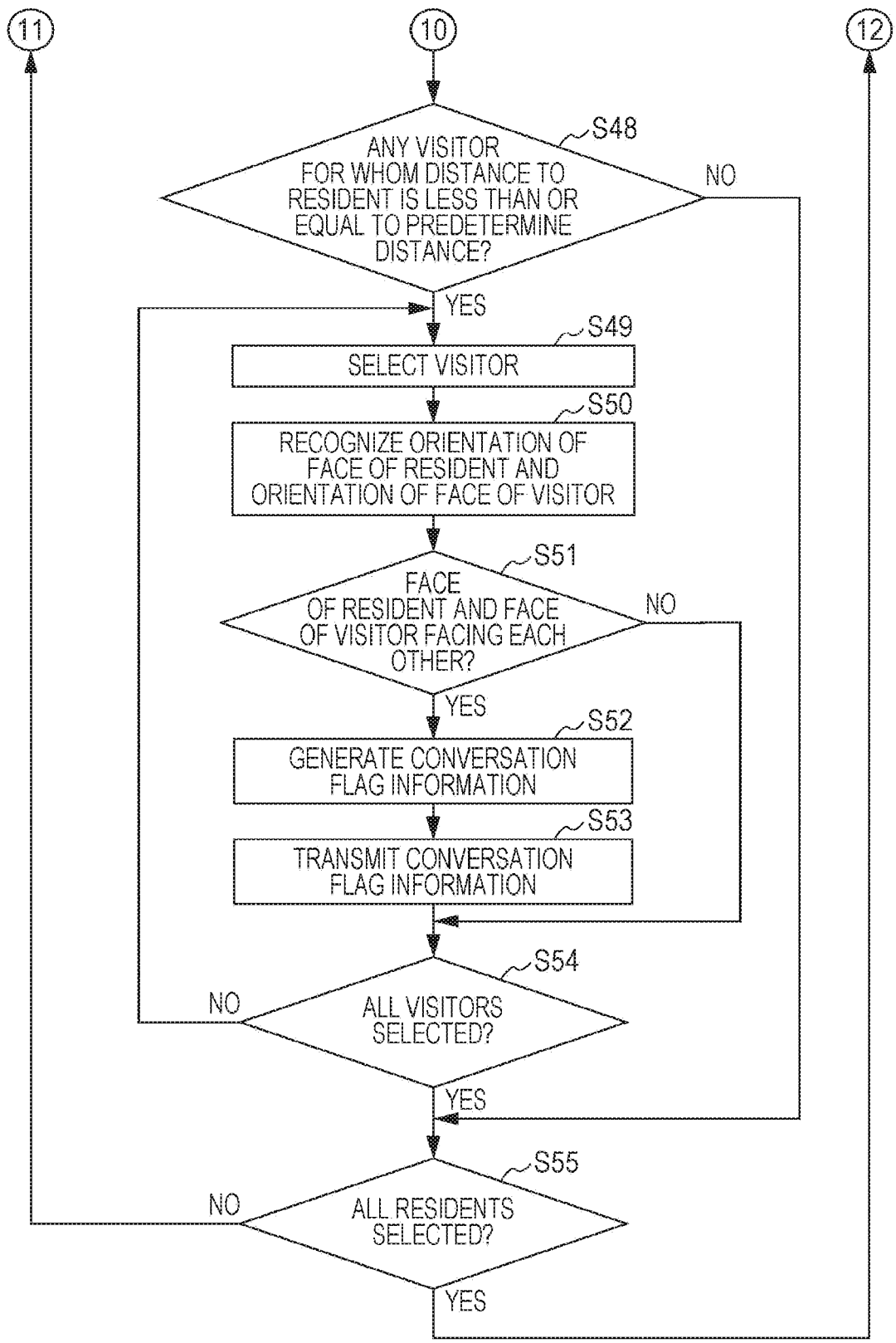
FIG. 9 is a second portion of the flowchart illustrating the operation of the camera according to the second embodiment.

FIG. 8 is a first portion of a flowchart illustrating the operation of the camera 3 according to the second embodiment, and FIG. 9 is a second portion of the flowchart illustrating the operation of the camera 3 according to the second embodiment.

First, in step S41, the processor 33 determines whether power supply to the camera 3 is turned on. If it is determined that power supply to the camera 3 is turned off (NO in step S41), the process ends.

On the other hand, if it is determined that power supply to the camera 3 is turned on (YES in step S41), in step S42, the image capturing unit 31 captures an image of a predetermined space. The image capturing unit 31 stores image information of the captured image in the image storage unit 321. The image capturing unit 31 stores a moving image in the image storage unit 321.

Then, in step S43, the image processing unit 331 obtains the image information from the image storage unit 321.

Then, in step S44, the image processing unit 331 extracts the features of a person from the image information. The features of a person include, for example, the face, eyes, nose, mouth of a person in a room, the shape of the face, the sizes of the face, eyes, nose, and mouth, the height of the person, the clothes of the person, the orientation of the face, and the position of the person in the room.

Then, in step S45, the person classification unit 332 classifies a person contained in the image information as a resident of the facility or a visitor to the facility, from the person's features extracted by the image processing unit 331. A face image of each resident is pre-registered in the person information storage unit 322. If a face image of a person included in the image information, which is extracted by the image processing unit 331, matches any pre-registered face image, the person classification unit 332 classifies the person as a resident. If a face image of a person included in the image information, which is extracted by the image processing unit 331, does not match any pre-registered face image, the person classification unit 332 classifies the person as a visitor.

The person classification unit 332 may classify the person as a resident or a visitor by using a neural network model obtained in advance from machine learning.

Then, in step S46, the distance calculation unit 333 selects the resident classified by the person classification unit 332. If residents are classified by the person classification unit 332, the distance calculation unit 333 selects one of the residents. If a single resident is classified by the person classification unit 332, the distance calculation unit 333 selects the single resident. If no resident is classified by the person classification unit 332, that is, if the image information contains no resident, the process may return to step S41.

Then, in step S47, the distance calculation unit 333 calculates the distance between the selected resident and the visitor. If visitors are classified by the person classification unit 332, the distance calculation unit 333 calculates the distance between the selected resident and each of the visitors. In this case, the distance calculation unit 333 calculates the Euclidean distance between the center-of-gravity position of an area showing the resident and the center-of-gravity position of an area showing each of the visitors.

Then, in step S48, the conversation determination unit 335 determines whether there is any visitor for whom the distance to the selected resident is less than or equal to a predetermined distance on the basis of the distance calculated by the distance calculation unit 333.

If it is determined that there is no visitor for whom the distance to the selected resident is less than or equal to the predetermined distance (NO in step S48), the process proceeds to step S55.

On the other hand, if it is determined that there is any visitor for whom the distance to the selected resident is less than or equal to the predetermined distance (YES in step S48), in step S49, the conversation determination unit 335 selects a visitor for whom the distance to the selected resident is less than or equal to the predetermined distance. If there are visitors for whom the distances to the selected resident are less than or equal to the predetermined distance, the conversation determination unit 335 selects one of the visitors. For example, the conversation determination unit 335 selects one of the visitors who is the closest to the selected resident.

Then, in step S50, the face orientation recognition unit 334 recognizes the orientation of the face of the selected resident and the orientation of the face of the selected visitor on the basis of the image information. The orientation of the face of the resident and the orientation of the face of the visitor are represented by vectors, for example.

Then, in step S51, the conversation determination unit 335 determines whether the face of the selected resident and the face of the selected visitor are facing each other. The face of the resident and the face of the visitor need not be completely facing each other. The conversation determination unit 335 may determine that the face of the resident and the face of the visitor are facing each other when the angle defined by the vector indicating the orientation of the face of the resident and the vector indicating the orientation of the face of the visitor is less than or equal to a predetermined angle. If it is determined that the face of the selected resident and the face of the selected visitor are not facing each other (NO in step S51), the process proceeds to step S54.

On the other hand, if it is determined that the face of the selected resident and the face of the selected visitor are facing each other (YES in step S51), in step S52, the conversation determination unit 335 generates conversation flag information. The conversation flag information includes, for example, identification information such as a name and a number for identifying a resident having a conversation with a visitor, the place in which the resident is located, the current time, and visitor information indicating the features of the visitor. The conversation determination unit 335 outputs the generated conversation flag information to the communication unit 34.

Then, in step S53, the communication unit 34 transmits the conversation flag information generated by the conversation determination unit 335 to the infection risk notification apparatus 1A.

Then, in step S54, the conversation determination unit 335 determines whether all of the visitors for whom the distances to the selected resident are less than or equal to the predetermined distance have been selected. That is, if there are visitors for whom the distances to the selected resident are less than or equal to the predetermined distance, the conversation determination unit 335 determines whether there is any unselected visitor among the visitors. If it is determined that not all of the visitors for whom the distances to the selected resident are less than or equal to the predetermined distance have been selected (NO in step S54), the process returns to step S49.

In step S49, the conversation determination unit 335 selects a visitor for whom the distance to the selected resident is less than or equal to the predetermined distance and who remains unselected. For example, the conversation determination unit 335 selects a visitor from among the visitors in order from the closest to the selected resident.

On the other hand, if it is determined that all of the visitors for whom the distances to the selected resident are less than or equal to the predetermined distance have been selected (YES in step S54), in step S55, the conversation determination unit 335 determines whether all the residents classified by the person classification unit 332 have been selected. That is, if residents are classified by the person classification unit 332, the conversation determination unit 335 determines whether there is any unselected resident among the residents. If it is determined that not all of the classified residents have been selected (NO in step S55), the process returns to step S46.

On the other hand, if it is determined that all of the classified residents have been selected (YES in step S55), the process returns to step S41.

Figure 10:
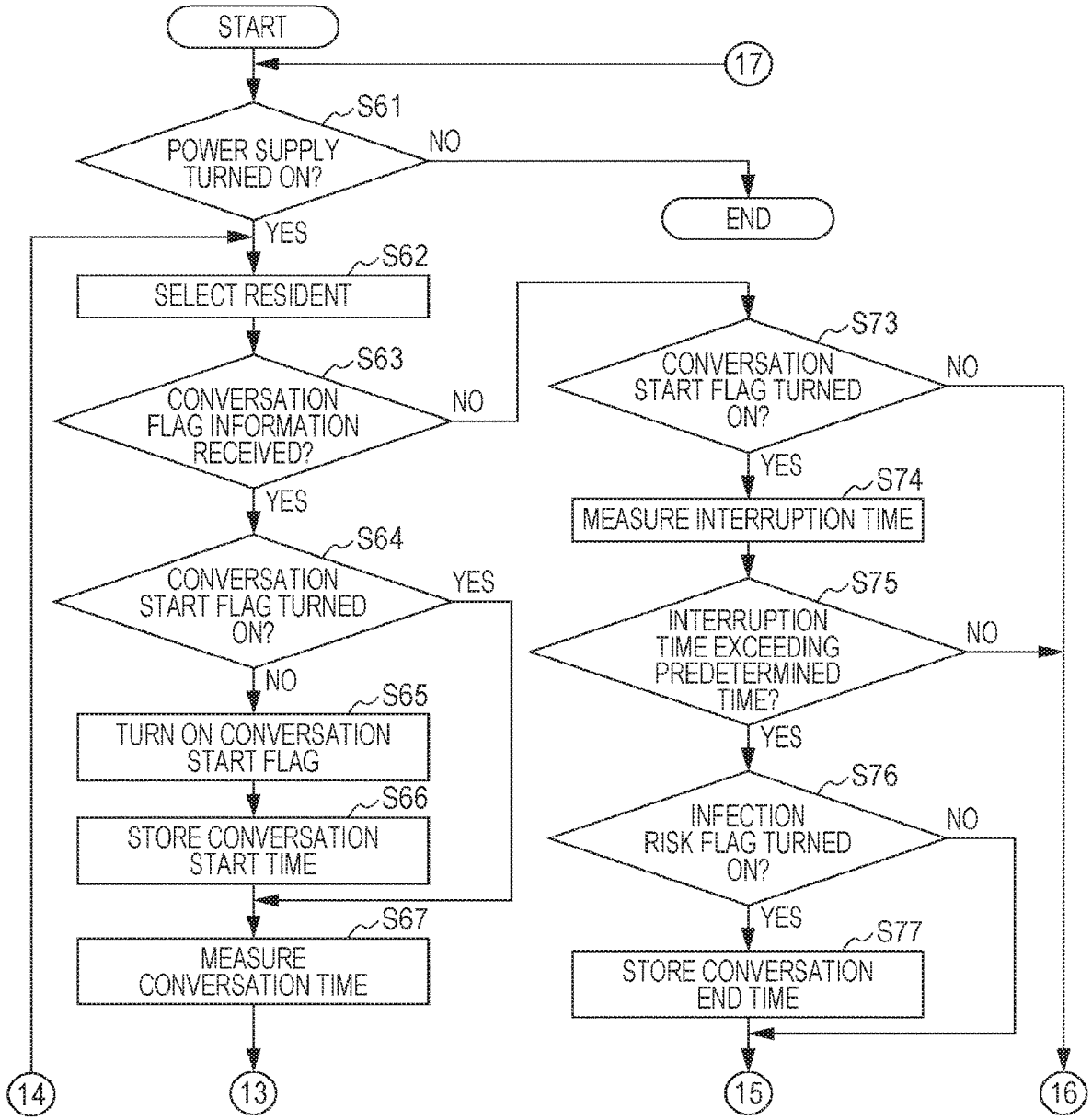
FIG. 10 is a first portion of a flowchart illustrating the operation of an infection risk notification apparatus according to the second embodiment.
Figure 11:
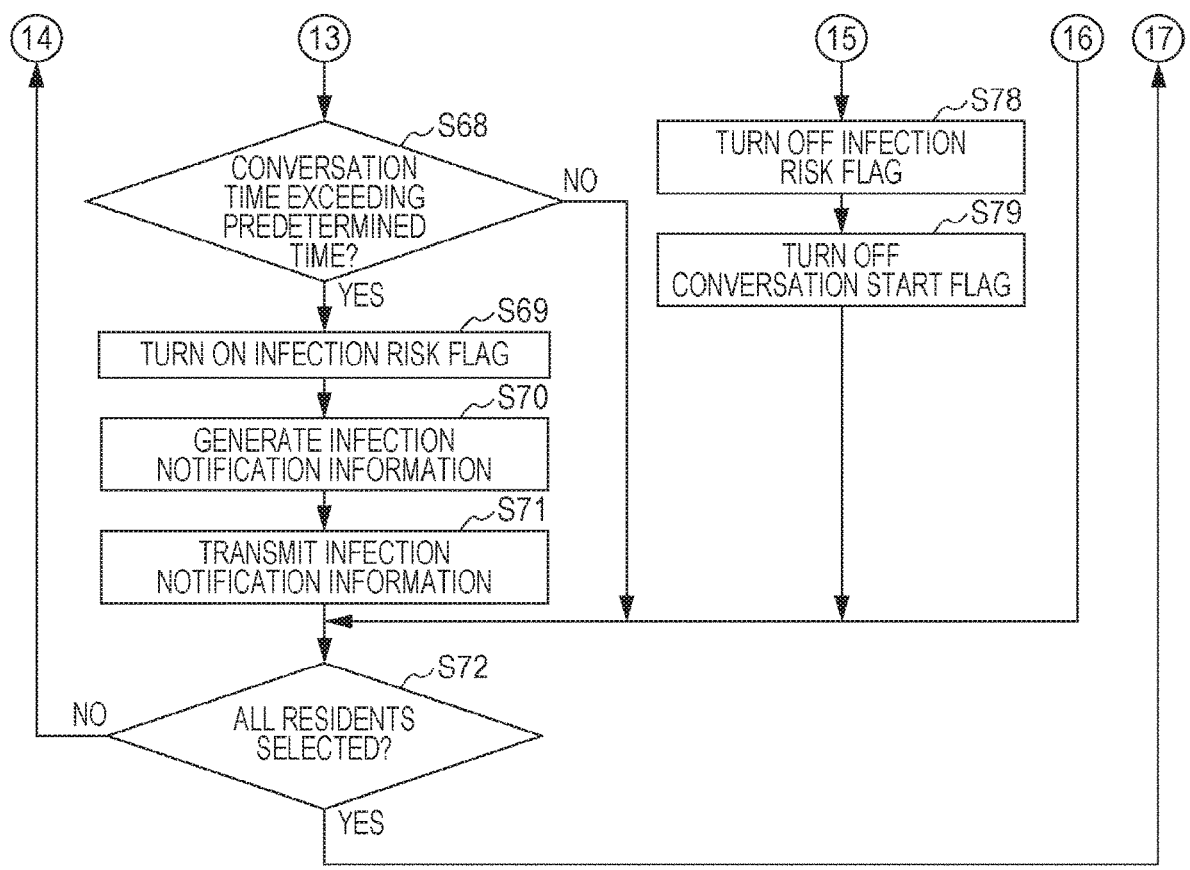
FIG. 11 is a second portion of the flowchart illustrating the operation of the infection risk notification apparatus according to the second embodiment.

FIG. 10 is a first portion of a flowchart illustrating the operation of the infection risk notification apparatus 1A according to the second embodiment, and FIG. 11 is a second portion of the flowchart illustrating the operation of the infection risk notification apparatus 1A according to the second embodiment.

First, in step S61, the processor 13A determines whether power supply to the infection risk notification apparatus 1A is turned on. If it is determined that power supply to the infection risk notification apparatus 1A is turned off (NO in step S61), the process ends.

On the other hand, if it is determined that power supply to the infection risk notification apparatus 1A is turned on (YES in step S61), in step S62, the conversation time measurement unit 136A selects one of the residents indicated by information stored in the resident information storage unit 124. The resident information storage unit 124 stores information on residents of the facility. The method for selecting a resident is not limited to any specific technique. For example, the conversation time measurement unit 136A selects a resident in order from the top of a list of residents, which is stored in the resident information storage unit 124.

Then, in step S63, the communication unit 14A determines whether the conversation flag information including the identification information of the selected resident has been received.

If it is determined that the conversation flag information including the identification information of the selected resident has been received (YES in step S63), in step S64, the conversation time measurement unit 136A determines whether the conversation start flag corresponding to the selected resident is turned on in the history information of the selected resident that is stored in the history information storage unit 123.

If it is determined that the conversation start flag corresponding to the selected resident is turned on (YES in step S64), the process proceeds to step S67.

On the other hand, if it is determined that the conversation start flag corresponding to the selected resident is not turned on (NO in step S64), in step S65, the conversation time measurement unit 136A turns on the conversation start flag corresponding to the selected resident.

Then, in step S66, the conversation time measurement unit 136A stores the current time in the history information storage unit 123 as the conversation start time.

Then, in step S67, the conversation time measurement unit 136A measures the conversation time during which the selected resident and the visitor are having a conversation with each other. Since the conversation start time is stored in the history information storage unit 123, the conversation time measurement unit 136A calculates a time period from the conversation start time to the current time to measure the conversation time during which the selected resident and the visitor are having a conversation with each other.

The processing of steps S68 to S71 illustrated in FIG. 11 is the same as the processing of steps S16 to S19 illustrated in FIGS. 3 and 4.

Then, in step S72, the conversation time measurement unit 136A determines whether all of the residents indicated by the information stored in the resident information storage unit 124 have been selected. That is, the conversation time measurement unit 136A determines whether there is any unselected resident among the residents indicated by information stored in the resident information storage unit 124. If it is determined that not all of the residents indicated by the information stored in the resident information storage unit 124 have been selected (NO in step S72), the process returns to step S62.

On the other hand, if it is determined that all of the residents indicated by the information stored in the resident information storage unit 124 have been selected (YES in step S72), the process returns to step S61.

If it is determined in step S63 that the conversation flag information including the identification information of the selected resident has not been received (NO in step S63), in step S73, the interruption determination unit 139 determines whether the conversation start flag corresponding to the selected resident is turned on in the history information of the selected resident that is stored in the history information storage unit 123.

If it is determined that the conversation start flag corresponding to the selected resident is not turned on (NO in step S73), the process proceeds to step S72.

On the other hand, if it is determined that the conversation start flag corresponding to the selected resident is turned on (YES in step S73), in step S74, the interruption time measurement unit 138 measures the interruption time during which the conversation between the resident and the visitor is interrupted. When starting the measurement of the interruption time, the interruption time measurement unit 138 stores in the memory 12 an interruption start time indicating the time of starting the measurement of the interruption time. Since the interruption start time is stored in the memory 12, the interruption time measurement unit 138 calculates a time period from the interruption start time to the current time to measure the interruption time during which the conversation between the resident and the visitor is interrupted.

Then, in step S75, the interruption determination unit 139 determines whether the measured interruption time exceeds a predetermined time. If it is determined that the measured interruption time does not exceed the predetermined time (NO in step S75), the process proceeds to step S72.

On the other hand, if it is determined that the measured interruption time exceeds the predetermined time (YES in step S75), in step S76, the interruption determination unit 139 determines whether the infection risk flag is turned on.

The processing of steps S76 to S79 illustrated in FIGS. 10 and 11 is the same as the processing of steps S25 to S28 illustrated in FIG. 3. After the processing of step S79, the process proceeds to step S72.

In this way, the camera 3 detects a conversation between a resident and a visitor, and the infection risk notification apparatus 1A measures the time during which the resident and the visitor are having a conversation with each other. If the risk of the resident contracting infectious disease is high, the terminal apparatus 2 is notified that the risk of the resident contracting infectious disease is high. This can simplify the configuration of an infection risk notification system and can reduce the cost of the infection risk notification system.

While apparatuses according to embodiments of the present disclosure have been described, the present disclosure is not limited to the embodiments. Various modifications conceivable by a person skilled in the art may be made to the embodiments, and components in different embodiments may be combined to form other embodiments without departing from the gist of the present disclosure. Such modifications and embodiments may also fall within the scope of one or more aspects of the present disclosure.

In the embodiments described above, the individual components may be implemented by dedicated hardware or may be implemented by executing a software program suitable for the individual components. The individual components may be implemented by a program execution unit such as a central processing unit (CPU) or a processor reading and executing a software program recorded on a recording medium such as a hard disk or a semiconductor memory.

Some or all of the functions of the apparatuses according to the embodiments of the present disclosure are typically implemented as a large scale integration (LSI) circuit, which is an integrated circuit. These functions may be formed by separate chips, or some or all of the functions may be formed into a single chip. The technique for circuit integration is not limited to LSI, and circuit integration may be implemented by using a dedicated circuit or a general-purpose processor. A field programmable gate array (FPGA) that is programmable after LSI manufacturing, or a reconfigurable processor capable of reconfiguring the connections and/or settings of circuit cells within LSI may be used.

Further, some or all of the functions of the apparatuses according to the embodiments of the present disclosure may be implemented by a processor such as a CPU executing a program.

The numbers used herein are for illustrative purposes only to provide a specific description of the present disclosure. The present disclosure is not limited to the illustrated numbers.

The order in which the steps in each of the flowcharts described above are performed is for illustrative purposes only to provide a specific description of the present disclosure, and may be changed so long as similar effects can be obtained. In addition, some of the steps described above may be executed simultaneously (or in parallel).

Various modifications conceivable by a person skilled in the art may be made to the embodiments of the present disclosure without departing from the gist of the present disclosure, and such modifications also fall within the scope of the present disclosure.

For example, embodiments of the present disclosure include the following information processing method.

An information processing method executed by a computer, including obtaining image information including a first image of a first person in a predetermined facility and a second image of a second person in the predetermined facility; classifying each of the first person and the second person as a resident of the facility or a visitor to the facility, the first person being classified as the resident, the second person being classified as the visitor; calculating a distance between the first person and the second person, based on the first image and the second image, measuring a time during which the distance is less than or equal to a predetermined distance; and transmitting, when the measured time exceeds a predetermined time, infection notification information indicating that a risk of the first person contracting infectious disease is high to a terminal apparatus.

An information processing method, a recording medium, and an information processing system according to embodiments of the present disclosure are suitable for use as an information processing method, a recording medium, and an information processing system that are capable of estimating the risk of a resident of a facility contracting infectious disease through conversation with a visitor and that issue a notification of the risk of contracting infectious disease.

What is claimed is:

1. A method executed by a computer, the method comprising:
    obtaining image information including a first image of a face of a first person and a second image of a face of a second person;
    calculating a distance between the first person and the second person, based on the first image and the second image;
    determining whether the first person and the second person are having a conversation with each other, based on the calculated distance;
    measuring, when it is determined that the first person and the second person are having a conversation with each other, a conversation time during which the first person and the second person are having a conversation with each other; and
    transmitting, when the measured conversation time exceeds a predetermined time, infection notification information indicating that a risk of the first person contracting infectious disease is high to a terminal apparatus,
    wherein the infection notification information includes a name of the first person and a feature of the second person.

2. The method according to claim 1,
    wherein the first image and the second image are captured with a camera installed in a predetermined facility.

3. A recording medium storing a program that, when executed by a computer, causes the computer to execute a process, the recording medium being a non-volatile computer-readable recording medium, the process comprising:
    obtaining image information including a first image of a face of a first person and a second image of a face of a second person;
    calculating a distance between the first person and the second person, based on the first image and the second image;
    determining whether the first person and the second person are having a conversation with each other, based on the calculated distance;
    measuring, when it is determined that the first person and the second person are having a conversation with each other, a conversation time during which the first person and the second person are having a conversation with each other; and
    transmitting, when the measured conversation time exceeds a predetermined time, infection notification information indicating that a risk of the first person contracting infectious disease is high to a terminal apparatus,
    wherein the infection notification information includes a name of the first person and a feature of the second person.

4. The recording medium according to claim 3,
    wherein the first image and the second image are captured with a camera installed in a predetermined facility.

5. A system comprising:
    a camera; and
    an apparatus, wherein
    the apparatus
    obtains image information from the camera, the image information including a first image of a face of a first person and a second image of a face of a second person,
    calculates a distance between the first person and the second person, based on the first image and the second image, determines whether the first person and the second person are having a conversation with each other, based on the calculated distance, measures, when it is determined that the first person and the second person are having a conversation with each other, a conversation time during which the first person and the second person are having a conversation with each other, and transmits, when the measured conversation time exceeds a predetermined time, infection notification information indicating that a risk of the first person contracting infectious disease is high to a terminal apparatus, wherein the infection notification information includes a name of the first person and a feature of the second person.

6. The system according to claim 5, wherein the first image and the second image are captured with the camera installed in a predetermined facility.

\* \* \* \* \*